United States Patent [19]

Banfield

[11] Patent Number: 5,308,613
[45] Date of Patent: May 3, 1994

[54] INDIRECT APHID CONTROL WITH LOW CONCENTRATION OF EBF

[75] Inventor: Michael G. Banfield, Bend, Oreg.

[73] Assignee: Consep Membranes, Inc., Bend, Oreg.

[21] Appl. No.: 945,841

[22] Filed: Sep. 16, 1992

Related U.S. Application Data

[63] Continuation of Ser. No. 669,678, Mar. 14, 1991, abandoned.

[51] Int. Cl.$^5$ ............................................. A01N 27/00
[52] U.S. Cl. ........................................ 424/84; 514/762; 514/919
[58] Field of Search .................... 514/762, 919; 424/84

[56] References Cited

U.S. PATENT DOCUMENTS 4,562,794  1/1986  Speckman ........................... 119/156

FOREIGN PATENT DOCUMENTS 8204249  12/1982  PCT Int'l Appl. ........... C07C 61/35

OTHER PUBLICATIONS

Chemical Abstracts, vol. 88:147466g (1978) abstracting Montgomery et al., "Comparative response of aphids . . . " Entomol. Exp. Appl. vol. 22(3), 1977, 236–242.
Edwards et al., "Trans-$\beta$-farnesene, Alarm Pheromone . . . ", Nature, vol. 241, 1973, pp. 126–127.
Webster's II New Riverside University Dictionary, The Riverside Publishing Company, 1984, p. 116.

Primary Examiner—Allen J. Robinson
Assistant Examiner—John D. Pak
Attorney, Agent, or Firm—Chernoff, Vilhauer, McClung & Stenzel

[57] ABSTRACT

An indirect control of aphids is disclosed, comprising the use of relatively minute concentrations of the pheromone E-$\beta$-farnesene, which prevents aphid-caused crop damage by warding off aphids and by attracting natural aphid predators and parasites.

5 Claims, 1 Drawing Sheet

INDIRECT APHID CONTROL WITH LOW CONCENTRATION OF EBF

This is a continuation of copending application(s) Ser. No. 07/669,678 filed on Mar. 14, 1991, which is now abandoned.

BACKGROUND OF THE INVENTION

Volatile chemicals used by insects for communication, known as semiochemicals, have been used for a number of years in the control of insect pests in agriculture. The use of semiochemicals for insect control offers a number of significant advantages over the use of chemical insecticides. Semiochemicals generally exhibit little toxicity toward humans and other nontarget organisms. Due to their volatility and instability caused by oxidation and photochemical degradation, they do not persist in the environment or leave detectable residues on treated crops.

It is known that many species of aphid communicate distress of various kinds by releasing a particular semiochemical known as an alarm pheromone. The principal constituent of the alarm pheromone for many of these aphids is the compound E-$\beta$-farnesene (EBF). Other lesser constituents of the alarm pheromone include the related farnesene isomers Z-$\beta$-, E-E-, E-Z-, Z-Z, and Z-E-$\alpha$-farnesenes. Studies of the behavior of aphids in the presence of vapors of EBF have shown that the typical aphid alarm symptoms include cessation of sucking and 25 dispersal away from the source of the pheromone. Wientjens et al., 29 Experientia 658 (1973). U.S. Pat. No. 4,505,934 discloses that 10 wt % solutions of EBF exhibit contact insecticidal action when applied topically to aphids. European patent application No. 0 266 822 discloses the use of EBF as an aphid control at concentrations exceeding that which causes the alarm reaction (1 to 10 ng/ml), teaching that concentrations exceeding 10 ng/ml cause a hormonal reaction that results in delayed or interrupted development of aphids and other insects. The principal drawback of both of these prior art uses of EBF is that both require relatively large amounts of the pheromone, which is very expensive.

What is needed, therefore, is an effective way to utilize EBF as an aphid control at relatively low concentrations. This need and others are met by the present invention, which is summarized and described in detail below.

SUMMARY OF THE INVENTION

It has been found that formulations of EBF alone or mixed with farnesene isomers, at concentrations well below those necessary for contact insecticidal action and even below those concentrations necessary for the aphid alarm response, are useful in mitigating crop damage due to aphids and in attracting aphid predators.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
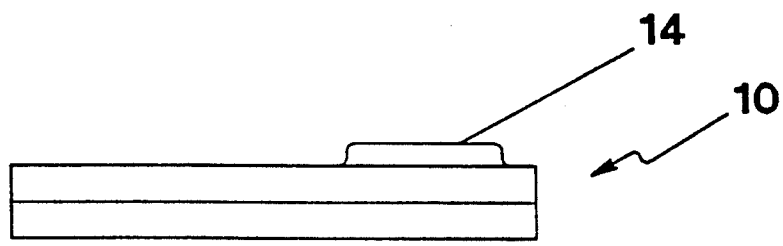
FIG. 1 is a side view of an exemplary controlled release dispenser suitable for use in the present invention.

According to the present invention, there is provided a method of mitigating crop damage due to aphids, comprising maintaining in the vicinity of the crop an active ingredient comprising E-$\beta$-farnesene in a concentration less than or equal to 0.25 ng per ml of air. In a closely related aspect, there is also provided a method of attracting natural predators of aphids to an area, comprising maintaining in the area an active ingredient comprising E-$\beta$-farnesene in a concentration less than or equal to 0.25 ng per ml of air.

It has been found that the maintenance of the above-mentioned relatively minute concentrations of EBF compositions in a given vicinity is effective in mitigating crop damage due to aphids by substantially reducing their numbers, and by attracting their natural predators. The EBF composition may be used in the form of pure EBF (not readily commercially available) or as the principal constituent of a mixture of its related farnesene isomers Z-$\beta$-, E-E-$\beta$-, E-Z-$\alpha$-, Z-Z-$\alpha$- and Z-E-$\alpha$-farnesenes.

A particularly preferred method of maintaining such low concentrations is by use of controlled release dispensers comprising a reservoir to hold the active ingredient EBF and a nonporous continuous polymeric rate-controlling membrane over the reservoir, the membrane being capable of releasing EBF by diffusion at a substantially zero order rate of release over a sustained period ranging from several days to several weeks. The construction of such dispensers is taught in U.S. Pat. No. 4,562,794, the disclosure of which is incorporated herein by reference.

The porous reservoir portion of the controlled-release dispenser of the present invention is formulated preferably from porous polysulfones, nylons, polycarbonates, polyvinylidene chloride, polyvinylidene fluoride, polytetrafluoroethylene, cellulose, cellulose esters, regenerated cellulose, polyolefins, polyurethanes, cross-linked polyvinyl alcohols, epoxy resins, and polyvinyl chlorides having interconnected pores, the pores being appropriate in size to retain the active ingredient in liquid form in the reservoir by capillary action. An especially preferred class of materials is low ash content cellulosic filter paper.

The reservoir material should also be such that the active ingredient is essentially insoluble in the reservoir. In this manner, the only forces retaining the active ingredient in the reservoir are physical, rather than chemical forces such as would be the case if the active ingredient forces were appreciably soluble in the reservoir.

The diffusional release rate of EBF through the nonporous rate-controlling membrane can be conveniently adjusted to the desired value by techniques known in the art including varying the surface area, thickness and composition of the membrane. Exemplary materials for fabricating the polymeric rate-controlling membrane include polyethylene; polypropylene; polytetrafluoroethylene; ethylene/vinyl acetate copolymers; silicone rubbers; neoprene rubber; chlorinated polyethylene; polyvinyl chlorides; vinyl chloride copolymers with vinyl acetate; vinylidene chloride, ethylene, and propylene; polyethylene terephthalate; butyl rubber; epichlorohydrin rubbers; ethylene/vinyl alcohol copolymers; polystyrene/acrylonitrile copolymers; polyamides; polyurethanes; and polyesters.

The active ingredient may have a coloring agent added thereto so as to indicate the amount thereof remaining. Since EBF is sensitive to degradation by oxidation or by ultraviolet light, the reservoir or the rate-controlling membrane may contain additives such as ultraviolet light absorbers and antioxidants.

The dispenser preferably has a portion of its outer surface covered with an impermeable backing material so as to cause the active ingredient to be released, in the case of a disc shape, from one side only. A suitable impermeable backing film is a polyethylene-foil-paper laminate made by Lithotype Co. of South San Francisco, Calif. Another is a polyethylene-polyester laminate made and sold by 3M of St. Paul, Minn. under the name "Scotchpak 108".

Figure 2:
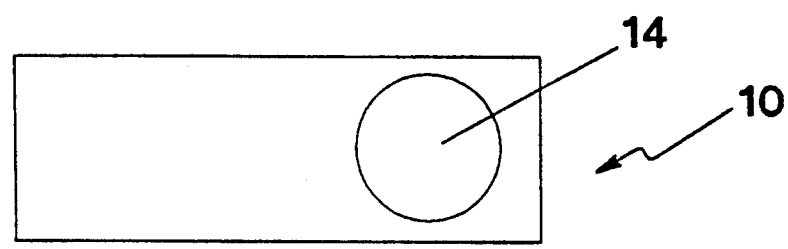
FIG. 2 is a plan view of the dispenser shown in FIG. 1.
Figure 3:
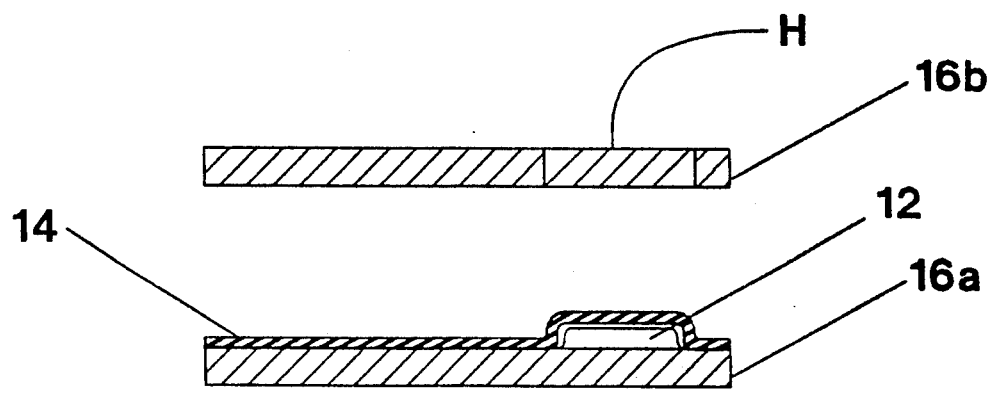
FIG. 3 is an exploded cross-sectional view of the dispenser shown in FIG. 1.

Referring to the drawings, an exemplary controlled release dispenser 10 is shown in FIGS. 1-3, comprising a reservoir 12 with a continuous nonporous polymeric rate-controlling membrane 14 over the reservoir, the reservoir being sandwiched between two impermeable members 16a and 16b, the topmost of the two having a hole punched therethrough at H. The laminated layers 16a, 14 and 16b are preferably sealed by heat except in the vicinity of reservoir 12.

EXAMPLE 1

A controlled release dispenser of the construction shown in FIGS. 1-3 was made by loading 10.0 mg of a commercially available EBF solution containing 55 wt % EBF and minor amounts of related farnesene isomers into a reservoir comprising a $1.8 \times 2.5$ cm piece of low ash content cellulosic Whatman #113 filter paper approximately 0.5 mm thick; placing the loaded reservoir on an impermeable polyester-polyethylene backing strip of Scotchpak 108; placing thereover a rate-controlling nonporous membrane of 4-mil-thick low density polyethylene; placing a second impermeable polyester-polyethylene strip over the rate-controlling membrane, the second strip having a hole punched through it in the vicinity of the reservoir; and heat-sealing the composite laminate except in the vicinity of the reservoir.

EXAMPLE 2

Another controlled release dispenser was made by loading the same amount of the same EBF composition as in Example 1 into a reservoir of approximately twice the size of low ash content cellulosic Ahlstrom ED-602-25 filter paper; placing the so-loaded reservoir onto an impermeable backing member of 1-mil-thick polyester film; placing over the reservoir a 5-mil-thick continuous nonporous rate-controlling membrane of polyurethane Tuftane 310 film; and heat-sealing the non-reservoir layers together except in the area of the reservoir.

EXAMPLE 3

The EBF composition release rates and % dispensation of four controlled release dispensers prepared according to Example 1 were measured by placing the devices in a temperature-controlled oven maintained at $25° \pm 1°$ C. for approximately 8 days and monitoring the weight of the dispenser as a function of time. The average release rate of EBF from the devices was $0.55 \pm 0.1$ mg/day, while the average dispensation was 75% of the original loading. The steady-state EBF composition concentration from a single device at a distance of 6.1 cm was calculated to be 0.55 ng/ml air.

EXAMPLE 4

The EBF composition release rates and % dispensation of four controlled release dispensers prepared according to Example 2 were measured in the same manner as in Example 1, and showed an average release rate of $0.29 \pm 0.02$ mg/day, with an average dispensation of 70%.

EXAMPLE 5

Controlled release dispensers prepared in accordance with Example 1 were field-tested in a pecan orchard in Pecos County, Tex. by placing 3 or 4 devices in each tree on selected branches midway between the ground and the top of the tree. Average maximum EBF concentration, not taking into account convection due to wind or photo-oxidation due to sunshine (which would have reduced the concentration), and assuming only molecular diffusion, was calculated to be 0.078 ng/ml in the vicinity of the treated trees. The populations of yellow pecan aphid (Monellia spp.) and black pecan aphid (*Tinocallis caryaefolieae*) were monitored on the day of treatment and 7 and 14 days thereafter. The number of yellow pecan aphids in the treated trees was reduced by 97% after 7 days and by 99% after 14 days; in the untreated trees, the number of yellow pecan aphids was reduced by 3% after 7 days and by 36% after 14 days. The treated trees were green and free from honeydew from aphid feeding. The untreated trees were all sticky with honeydew, had suffered a greater degree of defoliation than the treated trees, and were still infested with yellow pecan aphids at 14 days. Significant numbers of syrphid larvae, natural predators of aphids, were observed on the treated trees, while no syrphid larvae were seen on the untreated trees.

EXAMPLE 6

Controlled release dispensers prepared in accordance with Example 1 were field-tested in a watermelon patch in Pecos County, Tex. by attaching one dispenser to each of three wooden stakes driven into the ground at ten foot intervals adjacent to each plant to be treated. Average maximum EBF concentration, calculated in the same manner as in Example 5, was 0.21 ng/ml air in the vicinity of the treated plants. The populations of cotton/melon aphid (*Aphis gossypii*) on the treated plants and on an untreated plant were monitored on the day of treatment and 7 and 14 days thereafter. On the 7th day, the aphid population in the untreated plant had increased by 184%, while the average population in the treated plants had decreased by 77%. By the 14th day, the aphid populations in the untreated plant and in the treated plants were approximately 50% of their initial levels. However, the treated plants were green and free of honeydew, while the untreated plant was black, wilted, sticky with honeydew, and dying. On the 21st day, only the treated plants were alive. Large numbers of syrphid larvae were observed feeding on the aphids on nearly every leaf examined on the treated plants, while no larvae were seen on the untreated plant.

EXAMPLE 7

Controlled release dispensers prepared in accordance with Example 1 were field-tested in a field in Pima cotton in Reeves County, Tex. by attaching one device to each of three plants in the center of an area to be treated. Average maximum EBF concentration calculated in the same manner as in Example 5, was 0.33 ng/ml. The populations of cotton/melon aphid (*Aphis gossypii*) were monitored in the treated areas and in an untreated area of the same size. The aphid population in the untreated area dropped 43% by the 7th day and 94% by the 14th day, apparently due to natural causes. In the treated area the population was reduced by 68% after 7 days and was not significantly different from the untreated area after 14 days. Three days after treatment it was observed that all honeydew production by infesting aphids in the treated areas had ceased; honeydew production was not resumed in the treated areas during the duration of the test (14 days). The few remaining aphids on the treated plants were listless and not feeding. In the untreated area honeydew was observed on the leaves even after the aphid population dropped to low levels. Large numbers of syrphid larvae were observed feeding on the aphids on nearly every leaf examined on the treated plants, while no such larvae were seen on the untreated plants.

EXAMPLE 8

Controlled release dispensers prepared in accordance with Example 2 were field-tested by placing one dispenser at the center of a radius circular array of plants that had been artificially infested with aphids. The calculated maximum EBF concentration in the vicinity of the plants was 0.033 ng/ml. One day after treatment the number of *Lysiphlebus testaceipes* on nearby plants in the treated area had increased by more than 300%. (*Lysiphlebus testaceipes* are natural parasitic enemies of aphids in that they inject their eggs into the bodies of aphids, and the resulting wasp larvae consume the aphids.)

EXAMPLE 9

Controlled release dispensers prepared in accordance with Example 2 were field-tested in two trials in pecan orchards in El Paso, Tex. by placing one, two and three dispensers per tree in each of three groups of trees in both trials. In the first trial, with average maximum EBF concentrations of 0.043, 0.085 and 0.13 ng/ml, the average yellow aphid population in the treated trees 14 days after treatment was less than half the population in the untreated trees. In the second trial, with the same average maximum EBF concentrations as in the first trial, the average yellow aphid population in the treated trees 14 days after treatment was less than 20% of the population in the untreated trees.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:

1. A method of increasing the number of the aphid predator syrphid larvae or the aphid parasite *Lysiphlebus testaceipes* to combat aphids comprising maintaining in the vicinity of an area where said predator or parasite is present an effective amount of active ingredient comprising E-β-farnesene.

2. The method of claim 1 wherein the means of maintaining the amount of said active ingredient is a controlled release dispenser.

3. The method of claim 2 wherein said dispenser comprises a reservoir for said active ingredient and a continuous nonporous rate-controlling membrane over said reservoir.

4. The method of claim 1 wherein said active ingredient consists essentially of E-B-farnesene and its isomers.

5. The method of claim 4 wherein said isomers are selected from the group consisting of Z-β-, E-E-α-, E-Z-α-, Z-Z-α-, and Z-E-α-farnesenes.

* * * * *

UNITED STATES PATENT AND TRADEMARK OFFICE
CERTIFICATE OF CORRECTION

PATENT NO. : 5,308,613

DATED : May 3, 1994

INVENTOR(S) : Michael G. Banfield

It is certified that error appears in the above-indentified patent and that said Letters Patent is hereby corrected as shown below:

Col. 2, line 26: delete "E-E-$\beta$-" and insert -- E-E-$\alpha$- --

Col. 6, line 35, claim 4: delete the "B" between "E-" and "-farnesene" and substitute "$\beta$".

Signed and Sealed this

Twentieth Day of September, 1994

Attest:

BRUCE LEHMAN

Attesting Officer     Commissioner of Patents and Trademarks